United States Patent [19]

Shikai et al.

[11] Patent Number: 5,171,468

[45] Date of Patent: * Dec. 15, 1992

[54] AROMATIC POLYISOCYANATE

[75] Inventors: Kiyoshi Shikai, Tokyo; Ryuzi Haseyama, Kanagawa; Kouzou Hayashi, Kanagawa; Katsuyoshi Sasagawa, Kanagawa; Akihiro Yamaguchi, Kanagawa, all of Japan

[73] Assignee: Mitsui Toatsu Chemicals, Incorporated, Tokyo, Japan

[ * ] Notice: The portion of the term of this patent subsequent to Jun. 26, 2009 has been disclaimed.

[21] Appl. No.: 773,787

[22] Filed: Oct. 11, 1991

Related U.S. Application Data

[63] Continuation of Ser. No. 318,756, Mar. 3, 1989, abandoned.

[30] Foreign Application Priority Data

Mar. 10, 1988 [JP] Japan ................................. 63-55043

[51] Int. Cl.⁵ .......................................... C07C 119/048
[52] U.S. Cl. ............................. 252/182.21; 252/182.2; 525/509; 560/359
[58] Field of Search .............. 525/509; 560/359; 564/315; 252/182.2, 182.21

[56] References Cited

U.S. PATENT DOCUMENTS

| | | | |
|---|---|---|---|
| 3,180,883 | 4/1965 | Case | 560/359 |
| 3,267,145 | 8/1966 | Lund et al. | 564/315 |
| 3,344,162 | 9/1967 | Rowton | 564/315 |
| 3,424,795 | 1/1969 | Lund et al. | 564/315 |
| 3,530,152 | 9/1970 | Tokoli | 564/315 |
| 3,904,666 | 9/1975 | Schnabel et al. | 560/359 |
| 4,349,484 | 9/1982 | Merger et al. | 252/182.2 |
| 4,650,899 | 3/1987 | Kervennal et al. | 560/359 |
| 4,937,318 | 6/1990 | Yamaguchi et al. | 528/422 |
| 5,051,494 | 9/1991 | Yamaguchi | 528/422 |

FOREIGN PATENT DOCUMENTS 57-54153 7/1982 Japan ................................. 560/359

OTHER PUBLICATIONS

Fieser et al., *Advanced Organic Chemistry*, p. 617, Reinhold Publ. Corp. (1961) New York.
Ghatge et al., *Indian Chem. J.*, 13 (9), pp. 24–30 (1979).

*Primary Examiner*—Edward A. Miller
*Attorney, Agent, or Firm*—Burns, Doane, Swecker & Mathis

[57] ABSTRACT

Disclosed herein are a polyiscoyanate comprising a mixture of aromatic polyisocyanates represented by the general formula:

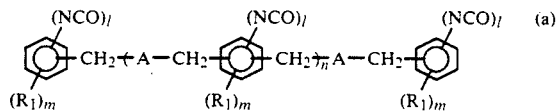

wherein A is a phenylene group, alkylene group, alkyl-substituted phenylene group, diphenylene group, diphenyl ether group or naphthylenyl group, $R_1$ is a halogen atom, lower alkoxy group with a carbon number of 4 or less or lower alkyl group with a carbon number of 5 or less, $R_1$s may be the same or different from each other and may form a ring, l is 1 or 2, m is an integer of 0–3, and n is a integer of 0–300, and a production process thereof.

8 Claims, 2 Drawing Sheets

AROMATIC POLYISOCYANATE

This application is a continuation of application Ser. No. 07/318,756, filed Mar. 3, 1989, now abandoned.

BACKGROUND OF THE INVENTION

1. Field of the Invention

This invention relates to an aromatic polyisocyanate and a production process thereof. The polyisocyanate of the present invention is a polyisocyanate having a novel structure and used as raw materials for polyurethane resins and polyurea resins in a wide variety of fields such as foams, elastomers, synthetic leathers, adhesives and films.

2. Description of the Related Art

Among the aromatic polyisocyanates known in the art, polyphenylmethane-polyisocyanate (hereinafter referred to as P-MDI) represented by the following general formula:

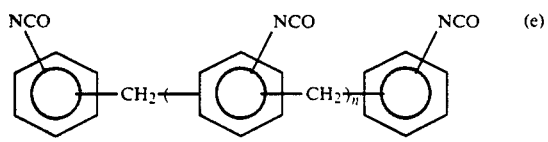

is widely-known and has been finding versatile uses as raw materials for polyurethane resins and polyurea resins.

SUMMARY OF THE INVENTION

The first object of the present invention is to provide a novel aromatic polyisocyanate which is entirely different in structure from P-MDI and expected to have new uses as raw materials for polyurethane resins and polyurea resins.

The second object of the present invention is to provide a novel production process of the above polyisocyanate.

In order to attain the above objects, the inventors have made intensive investigations, and finally found that the objects of the present invention can be attained by reacting an aromatic amine resin having a specific structure or a salt thereof with phosgene. The present invention has been completed on the basis of this finding.

Specifically, the novel polyisocyanate of the present invention is a polyisocyanate comprising a mixture of aromatic polyisocyanates represented by the general formula:

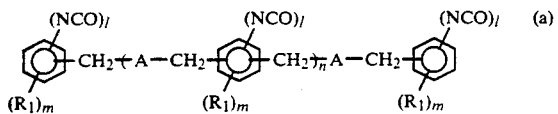

wherein A represents a phenylene group, alkylene group, alkyl-substituted phenylene group, diphenylene group, diphenyl ether group, or naphthylenyl group, $R_1$ is a halogen atom, lower alkoxy group with a carbon number of 4 or less or lower alkyl group with a carbon number of 5 or less, $R_1$s may be the same or different from each other and may form a ring, l means 1 or 2, m is an integer of 0-3, and n is an integer of 0-300.

Further, the novel production process of the present invention is a production process of a polyisocyanate comprising a mixture of aromatic polyisocyanates represented by the general formula (a), which process comprises reacting an aromatic amine resin comprising a mixture of aromatic amine compounds represented by the general formula:

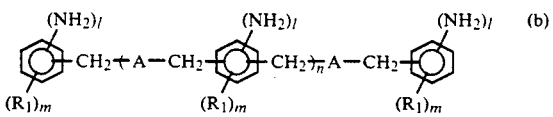

wherein A, $R_1$, l, m and n have in the general formula (a), or a salt thereof, with phosgene.

DETAILED DESCRIPTION OF THE INVENTION

Figure 1:
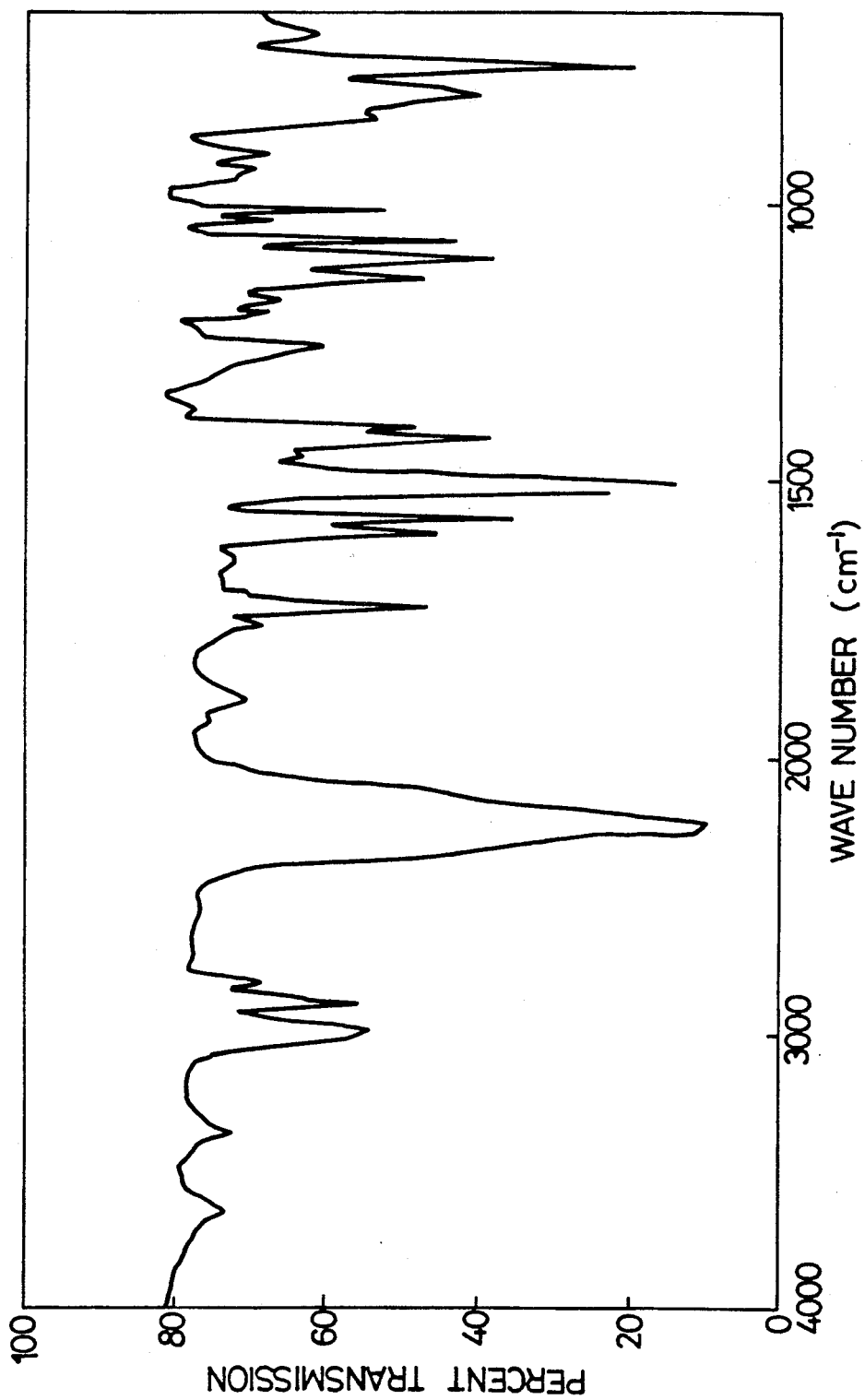
FIG. 1 is the IR spectrum of polyparaxylylene-polyphenyl-polyisocyanate obtained in Example 1.

The aromatic amine resins represented by the general formula (b) are entirely novel compounds which have been developed recently, and their properties and production processes are described in detail in Japanese patent application Ser. Nos. 252517/1987 and 282048/1987 (see U.S. Pat. No. 4,937,318 at column 3, lines 8-43, and the disclosure therein extending from column 4, line 57 to column 10, line 21).

The aromatic polyisocyanate of the present invention is prepared by reacting the aromatic amine resin represented by the foregoing general formula (b) directly with phosgene or by synthesizing a salt of the aromatic amine resin such as its hydrochloride in advance and suspending the salt in an inert solvent so that it is reacted with phosgene.

The former process is called "cold-hot two stage phosgenation", and the embodiment of the reaction suffers from no particular restriction. In general, however, gaseous phosgene is introduced into an inert solvent in a reactor, in which the reaction system can fully be stirred and which is provided with a phosgene gas inlet, while cooling the reaction system at a temperature of 0°-5° C. Thus, the phosgene is dissolved in the inert solvent almost to the saturated solubility of phosgene to the solvent. Then, a solution formed separately by dissolving the above-described amine resin in the inert solvent is added thereto while introducing gaseous phosgene in an amount 1 to 2 times as much as its stoichiometric quantity. In the mean time, the temperature of the reaction liquid is maintained at not higher than 15° C., and the hydrogen chloride thus-evolved and excess phosgene are purged out through a reflux condenser to the outside of the system. The contents in the reactor form a slurry. The main reaction is the formation of carbamyl chloride and amine hydrochlorides. After the addition of the amine solution, the reaction is continued for 30 minutes to 2 hours. The above-described procedure is referred to as cold phosgenation.

Then, the reaction system is heated to a temperature of 130° C. to 160° C. for 30 minutes to 3 hours. Upon raising temperature, the phosgene dissolved in the solvent is liable to vaporize and foam, so that it is preferable to reduce the feed rate of phosgene to the order of its theoretical quantity, as opposed to the case of cold phosgenation. After the temperature has been raised, the reaction is continued for 1 to 3 hours. When the slurry is entirely dissolved, the reaction is assumed to be complete. The above procedure is called hot phosgenation. The principal reactions of the hot phosgenation are the decomposition of carbamyl chloride to isocyanate and the phosgenation of amine hydrochlorides into isocyanates.

After completion of the hot phosgenation, the reaction system is heated to a temperature of 150°-180° C. and gaseous nitrogen is blown into the reaction system at an appropriate rate, (i.e., not lower than 200 ml/min.; this value varies depending on the reaction scale) to remove dissolved gaseous components and decompose sufficiently unreacted carbamyl chloride. Then, following cooling, the inert solvent is removed under reduced pressure by distillation to obtain an aromatic polyisocyanate.

The latter process is referred to as "phosgenation of amine hydrochloride". The hydrochloride of the above-described aromatic amine resin is synthesized in advance. The synthesis of the hydrochloride is effected with ease by the well-known method of treating an aromatic amine resin with hydrogen chloride or conc. hydrochloric acid. The thus-formed aromatic amine hydrochloride, which has been fully dried and pulverized, is dispersed in an inert solvent in a reactor equipped similarly to that used in the "cold-hot two stage phosgenation" process as described above. The reaction system is maintained at a temperature of 80°-160° C., to which system gaseous phosgene is admitted for 3 to 10 hours so that the total phosgene introduction may amount to 2 to 10 times as much as its stoichiometric quantity, thus synthesizing an isocyanate. The progress of the reaction may be inferred by the amount of gaseous hydrogen chloride evolved, the dissipation of the aromatic amine hydrochloride used as the raw material and insoluble in the inert solvent, and the transparency and homogeneity of the reaction liquid. The hydrogen chloride evolved and excess phosgene are discharged through a reflux condenser to the outside of the reaction system. After the reaction has been completed, gaseous nitrogen is introduced into the reaction solvent to remove dissolved phosgene, and subsequent to cooling and filtration, the inert solvent is distilled out under reduced pressure to obtain an aromatic polyisocyanate.

It is sufficient to introduce phosgene in an amount 2 to 10 times as much as its stoichiometric quantity for the both processes of "cold-hot two stage phosgenation" and "phosgenation of amine hydrochloride". As the inert solvent may be mentioned aromatic hydrocarbons, fatty acid esters and chlorinated aromatic hydrocarbons. Of these, orthodichlorobenzene is preferred.

The present invention will be illustrated by reference to the following examples. These examples are intended to illustrate the invention and are not to be construed to limit the scope of the invention. In the examples, description will be made particularly with regard to polyparaxylylene-polyphenyl-polyisocyanate of the following formula (c):

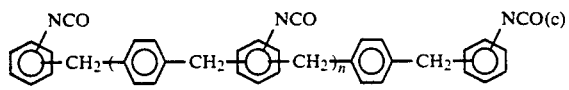

which is the compound of the general formula (a) wherein A is a p-phenylene group, m is 0, and l is 1.

EXAMPLE 1

Polyparaxylylene-polyaniline represented by the following formula:

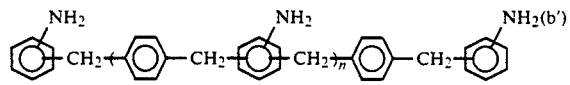

was used as a raw material for phosgenation. The molecular weight distribution of the polyaniline resin used as the raw material was determined with a high speed liquid chromatography using GPC column. The determination revealed that the distribution was 76.3 wt. % for the compound of the general formula (b') wherein $n=0$, 18.7 wt. % for the compound wherein $n=1$, 4.3 wt. % for the compound wherein $n=2$ and 0.7 wt. % for the compounds wherein $n=3$ or more. The mean molecular weight was about 350, while the amine equivalent of the resin was 0.653 eq/100 g according to the perchloric acid-glacial acetic acid method.

Into a 2-l reaction flask equipped with a stirrer, thermometer, phosgene inlet, cooling tube and dropping funnel, 682 g of orthodichlorobenzene (ODCB) were charged. The reaction flask was placed in a ice-water bath under stirring so that the inner temperature of the flask was kept at 1°-2° C. Then, gaseous phosgene was introduced therein at a rate of 100 g/hour for 2 hours. Subsequently, a solution of 100 g of the abovedescribed polyaniline resin in 704 g of orthodichlorobenzene was added dropwise over 45 minutes. Gaseous phosgene was also introduced therein at a rate of 100 g/ hour during the dropping. The temperature was 2°-8° C. at this moment. Then, with gaseous phosgene introducing at a rate of 100 g/hour, cold phosgenation was carried out at 4°-5° C. for 30 minutes. The cold phosgenation produced a yellowish-green slurry in the reaction flask due to the formation of carbamyl chloride and amine hydrochlorides. The reaction flask was heated with a mantle heater to raise the temperature to 140° C. over about 45 minutes. During the rise in temperature, gaseous phosgene was charged at a rate of 100 g/hour. In the course of raising temperature, the slurry was completely dissolved in orthodichlorobenzene with violent evolution of gaseous hydrogen chloride. Then, hot phosgenation was conducted at 140° C. for 75 minutes while introducing gaseous phosgene at a rate of 100 g/hour. A total of 525 g of gaseous phosgene was introduced by the cold-hot two state phosgenation. This amount was equivalent to 8.1 times as much as the theoretical value. Then, the reaction liquid was raised in temperature to 160° C., following which gaseous nitrogen was admitted thereto at a rate of 500 ml/min. for 2 hours to remove dissolved gaseous components and decompose fully unreacted carbamyl chloride. After cooling, a bit of undissolved matters by filtration and then orthodichlorobenzene by distillation under reduced pressure (about 1 mm Hg abs.) were removed from the reaction liquid. Thus, 119.8 g of polyparaxylylene-polyphenyl-polyisocyanate were obtained. Its analysis revealed that it had an NCO% of 23.5% by weight (theoretical value: 23.5% by weight), a hydrolyzable chlorine content of 0.28% by weight, an acid content of 0.063% by weight and a residual ODCB content of 47 ppm by weight.

The IR spectrum of the aromatic polyisocyanate is given in FIG. 1.

EXAMPLE 2

By the procedure of vacuum distillation, 30 g of the aromatic polyisocyanate obtained in Example 1 was purified. About 20 g of a yellowish transparent liquid were obtained under the conditions of boiling points of 210°–220° C./0.2 mmHg abs. and oil-bath temperatures for the distillation flask of 220°–240° C. The liquid product was rapidly solidified into a crystal with a melting point of 45°–48° C. As a result of the analyses described below, the liquid product was found to be paraxylylenediphenyl isocyanate, which is the compound represented by the formula (c) wherein n=0, the formula (c) representing the aromatic polyisocyanate obtained in Example 1.

| Elemental analysis ($C_{22}H_{16}N_2O_2$): | | | |
|---|---|---|---|
| | C | H | N |
| Calculated (%) | 77.63 | 4.74 | 8.23 |
| Found (%) | 77.86 | 4.35 | 8.25 |

Figure 2:
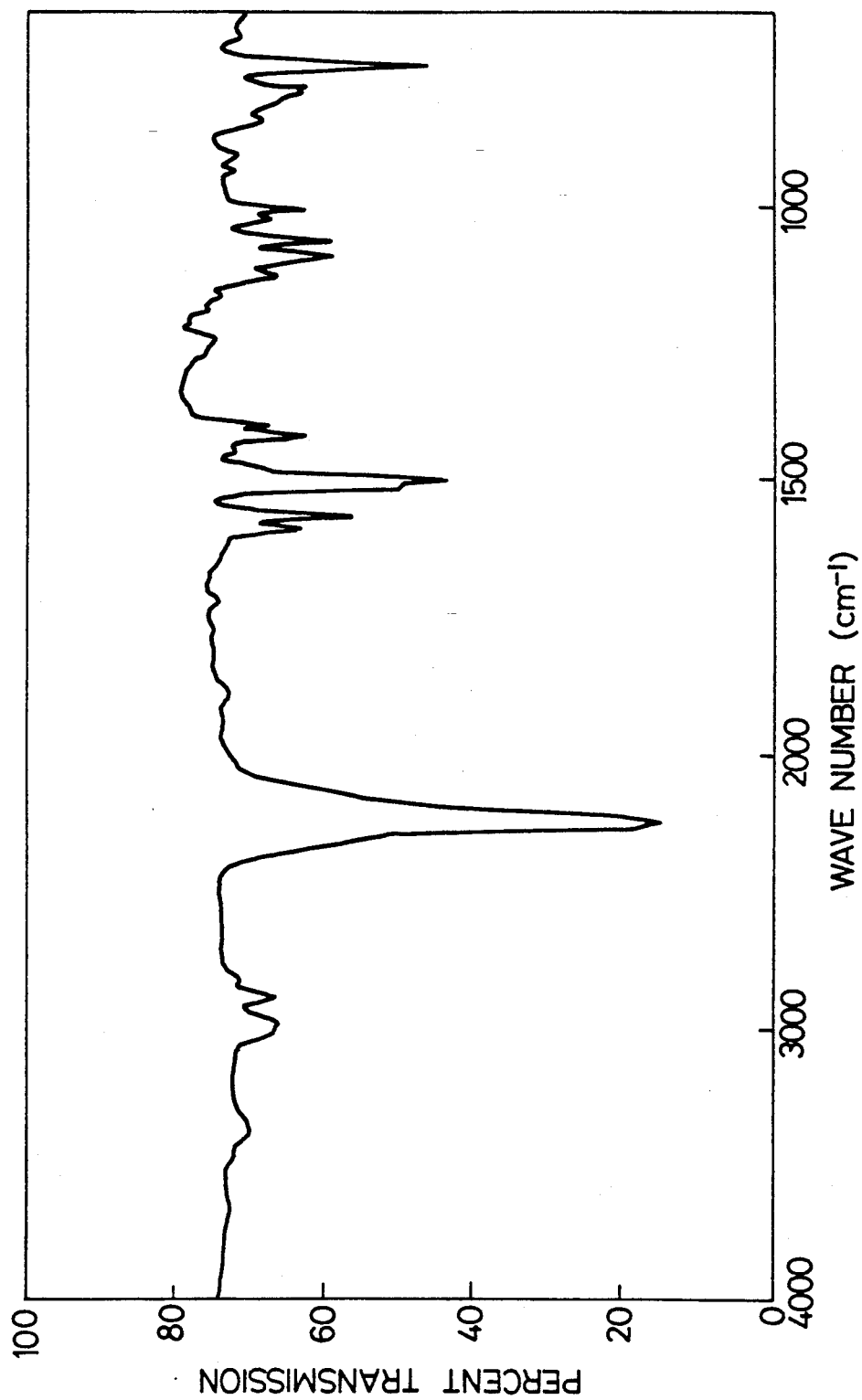
FIG. 2 is the IR spectrum of paraxylylenediphenyl isocyanate obtained in Example 2.

NCO % by weight: Found 24.65% (Calculated 24.69%)
IR spectrum: shown in FIG. 2
H-NMR (CDCl$_3$, TMS) ppm
δ 3.92 (4H —CH$_2$— × 2)
7.10 (12H Ph—H$_4$ , 3)

EXAMPLE 3

Phosgenation was carried out in the same manner as in Example 1 by using polyparaxylylene-polyaniline represented by the formula (b') as a raw material. The molecular weight distribution of the polyaniline resin used as the raw material was determined according to the same analytical procedure as in Example 1. The determination revealed that the distribution was 56.5 wt. % for the compound of the formula (b') wherein n=0, 26.5 wt. % for the compound wherein n=1, 10.1 wt. % for the compound wherein n=2, 5.6 wt. % for the compound wherein n=3, and 1.3 wt. % for the compounds wherein n=>4. The mean molecular weight was about 423, while the amine equivalent of the resin was 0.633 eq/100 g according to the perchloric acid-glacial acetic acid method.

In 704 g of orthodichlorobenzene were dissolved 100 g of the polyaniline resin, following which phosgenation was conducted in the same manner as in Example 1. A total of 400 g of gaseous phosgene was introduced in the cold-hot two stage phosgenation. This amount corresponded to 6.4 times that of the theoretical value. Subsequently, dissolved gaseous components were removed from the reaction liquid, and carbamyl chloride was decomposed substantially. Following cooling and filtration, orthodichlorobenzene was removed under reduced pressure by distillation, thereby obtaining 103.5 g of polyparaxylylene-polyphenyl-polyisocyanate. Its analysis clarified that it had an NCO% of 23.1% by weight, a hydrolyzable chlorine content of 0.41% by weight and an acid content of 0.10% by weight.

The aromatic polyisocyanates obtained in accordance with the process of the present invention are entirely novel compounds which have never been known in the art and hence are anticipated to have novel uses as raw materials for polyurethane resins and polyurea resins. Further, from the aromatic polyisocyanates and by the procedure of high-vacuum distillation, etc., there are obtained relatively low molecular aromatic polyisocyanates, namely, the compounds of the general formula (a) wherein A is a p-phenylene group, m is 0, l is 1, and n is 0 (i.e., aromatic diisocyanates). These are also absolutely novel compounds and expected to have new uses.

We claim:

1. A polyisocyanate mixture comprising an aromatic polyisocyanate represented by the general formula:

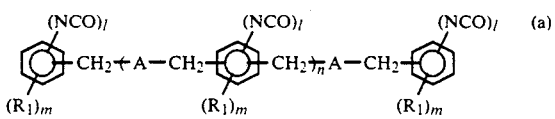

wherein A represents a phenylene group, alkyl-substituted phenylene group, diphenylene group, diphenyl ether group, or naphthylenyl group, R$_1$ is a halogen atom, lower alkoxy group with a carbon number of 4 or less or lower alkyl group with a carbon number of 5 or less, R$_1$s may be the same of different from each other and may form a ring, l means 1 or 2, m is an integer of 0–3, and n is an integer of 0–300 with the proviso that when A is a phenylene group n is at least 1.

2. The polyisocyanate as claimed in claim 1 wherein l is 1 and m is 0.

3. The polyisocyanate as claimed in claim 2 which comprises a mixture of aromatic polyisocyanates of formula (a) wherein each n is 0, 1, 2, 3 or 4.

4. The polyisocyanate as claimed in claim 3 wherein A is a phenylene group.

5. The polyisocyanate as claimed in claim 1 wherein A is a phenylene group.,

6. The polyisocyanate as claimed in claim 5 wherein l is 1 and m is 0.

7. The polyisocyanate as claimed in claim 1 wherein m is 2 or 3 and two of the R$_1$ groups join to form a 5–6 membered alicyclic ring which may have side chain(s).

8. The polyisocyanate as claimed in claim 5 wherein A is a p-phenylene group, and n is at least 1.

* * * * *

UNITED STATES PATENT AND TRADEMARK OFFICE
CERTIFICATE OF CORRECTION

PATENT NO. : 5,171,468
DATED : December 15, 1992
INVENTOR(S) : Shikai et al.

It is certified that error appears in the above-identified patent and that said Letters Patent is hereby corrected as shown below:

ON THE TITLE PAGE:

In the Abstract, line 1, delete "polyiscoyanate" and insert therefor --polyisocyanate--.

In column 6, line 34, delete "1" and insert therefor -- $\ell$ --;

line 39, delete "1" (first occurrence) and insert therefor -- $\ell$ --; and line 48, delete "1" (first occurrence) and insert therefor -- $\ell$ --.

Signed and Sealed this

Twenty-fifth Day of January, 1994

Attest:

BRUCE LEHMAN

*Attesting Officer*   *Commissioner of Patents and Trademarks*